United States Patent [19]

Stearns

[11] Patent Number: 5,074,149
[45] Date of Patent: Dec. 24, 1991

[54] ACOUSTIC WAVE MEASUREMENT OF THE PROPERTIES OF POROUS MATERIALS FILLED WITH AIR AND GRANULES

[75] Inventor: Richard G. Stearns, Mountain View, Calif.

[73] Assignee: Xerox Corporation, Stamford, Conn.

[21] Appl. No.: 675,400

[22] Filed: Mar. 26, 1991

[51] Int. Cl.$^5$ .......................................... G01N 29/00
[52] U.S. Cl. ....................................... 73/579; 73/597; 73/599; 118/689; 355/246
[58] Field of Search ........................ 355/203, 214, 246; 118/688, 689, 690, 694; 73/620, 624, 627, 290 V, 32 A, 579, 597, 599

[56] References Cited

U.S. PATENT DOCUMENTS

| | | | |
|---|---|---|---|
| 4,313,343 | 2/1982 | Kobayashi et al. | 73/290 V |
| 4,346,985 | 8/1981 | Watson et al. | 355/246 |
| 4,431,300 | 2/1984 | Snelling | 355/246 |
| 4,447,145 | 5/1984 | Snelling et al. | 355/203 |
| 4,804,996 | 2/1989 | Snelling | 355/203 |

FOREIGN PATENT DOCUMENTS

| | | | |
|---|---|---|---|
| 0149072 | 11/1981 | Japan | 355/203 |
| 0077462 | 5/1984 | Japan | 355/203 |

OTHER PUBLICATIONS

Biot, M. A., Theory of Propagation of Elastic Waves in a Fluid-Saturated Porous Solid, The Journal of the Acoustical Society of America, Mar. 1956; 28(2): 179-191.

Berryman, J. G., Confirmation of Biot's Theory, Applications Physics Letters, 15 Aug. 1980; 37(4): 382-384.

Attenborough, K., Acoustical Characteristics of Rigid Fibrous Absorbents and Granular Materials, The Journal of the Acoustical Society of America, Mar. 1983; 73(3): 85-799.

Attenborough, K., On the Acoustic Slow Wave in Air-Filled Granular Media, The Journal of the Acoustical Society of America, Jan. 1987; 81(1); 93-102.

Nagy, P. B., Adler, L., Slow Wave Propagation in Air-Filled Porous Materials and Natural Rocks, Applied Physics Letters, 18 Jun. 1990; 56(25); 2504-2506.

Primary Examiner—A. T. Grimley
Assistant Examiner—William J. Royer
Attorney, Agent, or Firm—Serge Abend

[57] ABSTRACT

A method for the situ measuring of a sample of a porous material having a gaseous fluid and fine granular material located within its pores and, in particular, for determining the concentration of the fine granular material within the sample. The method includes the steps of generating a first acoustic wave signal of known amplitude and phase velocity, directing the first acoustic wave signal through the sample, receiving a second acoustic wave signal representing the first acoustic wave having passed through the sample, and determining the concentration of the fine granular material in the sample from the changes between the first acoustic wave signal and the second acoustic wave signal.

9 Claims, 8 Drawing Sheets

ACOUSTIC WAVE MEASUREMENT OF THE PROPERTIES OF POROUS MATERIALS FILLED WITH AIR AND GRANULES

FIELD OF THE INVENTION

This invention relates to the use of acoustic waves to measure the properties of porous materials which are structural or comprised of granules and whose pores are filled with air and a fine granular material. More particularly, it relates to the measurement of multi-component granular mixtures, such as two-component developers as used in electrophotographic printing machines, and the in situ and non-invasive determination of toner concentration.

BACKGROUND OF THE INVENTION

Although this invention has broad application to the measurement of the ratio of fine granular material within a porous material, the following exemplary description will be specifically directed to the measurement of toner concentration in an electrophotographic machine. Generally, the process of electrophotographic printing includes the following series of process steps. (a) Charging a photoconductive member to a substantially uniform potential so as to sensitize its surface. (b) Exposing the charged photoconductive surface to a light image of an original document to be reproduced, thereby discharging lightstruck areas and recording an electrostatic latent image on the photoconductive member corresponding to the informational areas contained in the original document. (c) Developing the latent image by bringing a developer mixture into contact therewith, for forming a powder image on the photoconductive member. (d) Transferring the powder image to a copy sheet. (e) Permanently affixing (usually by heat) the powder image to the copy sheet.

A common type of developer mixture frequently used in electrophotographic printing machines comprises two components. The first component is carrier granules, usually on the order of 100 $\mu$m to 150 $\mu$m in diameter. The second component is toner particles, usually on the order of 10 $\mu$m in diameter. The toner particles are heavily loaded with pigment and adhere triboelectrically to the carrier particles for being transported thereby. When the mixture passes over the electrostatic latent image on the photoconductive member there is a preferential attraction of the toner particles for the latent image. Thus, during the printing process the toner particles are constantly being depleted from the developer mixture which must be replenished so as to maintain the required toner concentration, in the developer, typically, on the order of 4% to 7% by mass.

For high-quality printing, it is necessary to keep the mixture of toner and carrier well-controlled. If, for example, there is too little toner in the mixture, resulting images may be insufficiently dark. On the other hand, too much toner in the mixture may cause overly-dark images, or may produce unwanted contamination in the printer, as well as undesirable background on the image. As the quality demanded from printers continues to increase, it is expected that controlling the concentration of toner in the mixture will become ever more critical. This will be particularly true for obtaining high resolution, grey-level and color images.

Various techniques have been devised for measuring the toner in the mixture. One may measure the concentration of toner particles within a developer mixture or measure the developability of the developer mixture. Developability measurement actually deposits toner upon a test area so as to take into account, in addition to the toner concentration, environmental conditions, such as temperature and humidity, and other physical parameters, such as spacing, electrical bias, mass flow rate and magnetic field patterns. In each technique, any deviations from a desired state generates a signal which is used to control the addition of toner to the mixture, as necessary. Most commonly, concentration and developability sensing are accomplished by passing the developer over a surface to which the toner is attracted and optical means are used to generate the sensing signal.

Clearly, in an environment where toner powder is pervasive it would be desirable to avoid optical sensing. Therefore, it is an object of this invention to use an acoustic wave to directly measure toner concentration.

SUMMARY OF THE INVENTION

The method of the present invention enables the in situ measuring of a sample of a porous material having a gaseous fluid and fine granular material located within its pores for determining the concentration of the fine granular material within the sample. It may be carried out, in one form, by providing the steps of generating a first acoustic wave signal of known amplitude and phase velocity, directing the first acoustic wave signal through the sample, receiving a second acoustic wave signal representing the first acoustic wave having passed through the sample, and determining the concentration of the fine granular material in the sample from the changes between the first acoustic wave signal and the second acoustic wave signal.

THEORY OF OPERATION OF THE INVENTION

The "slow compressional wave" is a particular acoustic mode that is found in fluid filled porous solid media. The salient feature of this wave is that its phase velocity is lower than the compressional wave phase velocity in either the solid or fluid materials. When the fluid is a liquid, because of the reasonable acoustic coupling between the solid and liquid, there are a number of additional acoustic modes supported by the porous medium, for example, a faster compressional wave as well as a shear wave. This makes the measurement of the "slow compressional wave", which is always the smallest signal, quite difficult in liquid filled porous media. The situation is greatly simplified in a system where the fluid is a gas, such as air, since there is only one acoustic mode.

While the propagation properties of acoustic waves have been found to be useful in characterizing many materials, and the non-destructive evaluation of materials using ultrasonic acoustic waves is a well-developed field of study, "slow" acoustic waves have had a much more limited usage, primarily as a measuring tool in oil geology and oceanography for determining the porosity of solids filled with water. Although some studies have shown that "slow" wave propagation in air-filled porous materials and natural rocks can be used to study certain material properties such as tortuosity and permeability, there has been little applied use.

For an air filled porous medium, because of the very large impedance mismatch between air and the porous solid material, the solid material is basically rigid and the acoustic wave doesn't couple into it. A good approximation is that none of the acoustic energy in an air-filled porous medium is coupled into the porous solid. This phenomenon simplifies measurement of the "slow" wave in an air-filled porous medium, since there are no other bulk acoustic modes within the sample to obscure the measurement, and the slow compressional wave is the only acoustic mode present. The propagation of a compressional acoustic wave through an air-filled porous medium is affected by the viscosity of the air and the mechanical structure of the solid porous material. The viscosity causes the acoustic wave to attenuate dramatically at low frequencies. Of the several important quantities related to the structure, which affect the phase velocity of the wave, i.e., porosity, pore size, tortuosity and permeability, tortuosity is the most important at the higher frequencies, as will become apparent.

Porosity ($\Omega$) is a dimensionless quantity representative of the fraction of a crossectional area of the porous material that is filled with the fluid. In a granular mixture, it is an indication of how loosely packed or tightly packed it is. Thus, a path through a mixture of two granular materials in a gaseous fluid is a serpentine interstitial route around the solid particles and is a function of the porosity of the mixture.

It may be reasonably assumed that the solid particles are entirely rigid and fixed relative to the air around them, due to their much greater density and stiffness relative to the air. Since air is a viscous medium, it follows that at the surface of these fixed particles the air velocity in the acoustic wave must be zero, increasing to some finite value between the pores of the material. The following equation defines the viscous skin depth by its characteristic length (L), representing the distance from the surface of the solid material over which mechanical perturbations of frequency (f) are present when the acoustic field decays in a fluid of viscosity (v):

$$L = \left(\frac{v}{\pi f}\right)^{\frac{1}{2}} \quad (1)$$

If the pore size between granules of the porous medium is on the order of length (L), then the acoustic field within the pores is heavily influenced by the effects of viscosity and the acoustic wave actually becomes diffusive in nature, with large attenuation and dispersion.

In a toner/carrier mixture, if we assume the larger carrier granular material to be on the order of about 125 $\mu$m in diameter, the pore size might be about 15% of this, or about 19 $\mu$m. Equating this with the value of the viscous skin depth (L) in Equation 1, we find that there is a critical frequency ($f_c$) of about 13.5 kHz, below which the acoustic wave is severely affected by viscosity. For frequencies considerably larger than $f_c$, the viscous skin depth (L) becomes significantly smaller than the pore size, and the effect of viscosity on the propagation of the acoustic wave between the solid granules becomes smaller. Thus, it is preferred that the acoustic frequency be in the regime, $f > f_c$.

Tortuosity ($\alpha$) is also a dimensionless quantity (always greater than unity) representative of the ratio between the actual path length traversed by the "slow" acoustic wave through the porous material and the structural dimension of the material. It indicates that the microscopic flow of acoustic energy must wend its way through the porous medium. For the case of spherical particles, tortuosity ($\alpha$) can be related directly to the porosity ($\Omega$) of the granular medium, i.e., that fraction of a crossectional area of the material that is filled with air (always less than unity), by the equation:

$$a = \tfrac{1}{2}(1 + \Omega^{-1}) \quad (2)$$

It is known that in the limit of $f >> f_c$, the acoustic wave becomes entirely nondispersive, and its phase velocity (v) is dominated by the tortuosity of the mixture, as represented in the following equation:

$$v = v_g/\alpha^{\frac{1}{2}} \quad (3)$$

where $v_g$ represents the acoustic velocity in the bulk gas. It can be seen that the compressional wave phase velocity through the porous medium decreases as the tortuosity of the medium increases.

As the relative concentration of the smaller constituent in a two-component granular medium is increased, it fills the pores of the larger constituent, resulting in a decrease in porosity of the mixture. In the general case for spherical particles, as represented in Equation 2, tortuosity ($\alpha$) increases as the porosity of the medium ($\Omega$) decreases. Thus, it follows from Equation 3 that as porosity of the granular medium decreases and the tortuosity increases, the acoustic wave velocity in the medium should decrease (assuming an acoustic frequency $f > f_c$).

In accordance with the present invention, it is possible by measuring the acoustic wave velocity (at an acoustic frequency $f > f_c$) passing through a multi-component granular medium to determine the tortuosity of the mixture so as to infer the relative concentrations of the components in the mixture. It is to be understood that in general, one initially needs to calibrate the measurement by determining the acoustic wave phase velocity for samples of known relative concentration.

BRIEF DESCRIPTION OF THE DRAWINGS

Other objects and further features and advantages of this invention will be apparent from the following, more particular, description considered together with the accompanying drawings, wherein.

DETAILED DESCRIPTION OF THE INVENTION

While the present invention will hereinafter be described in connection with an electrophotographic apparatus and method, it should be understood that it is not intended to limit the invention to that environment. On the contrary, this invention has utility in the measurement of concentration of many air and granule filled porous materials.

Figure 1:
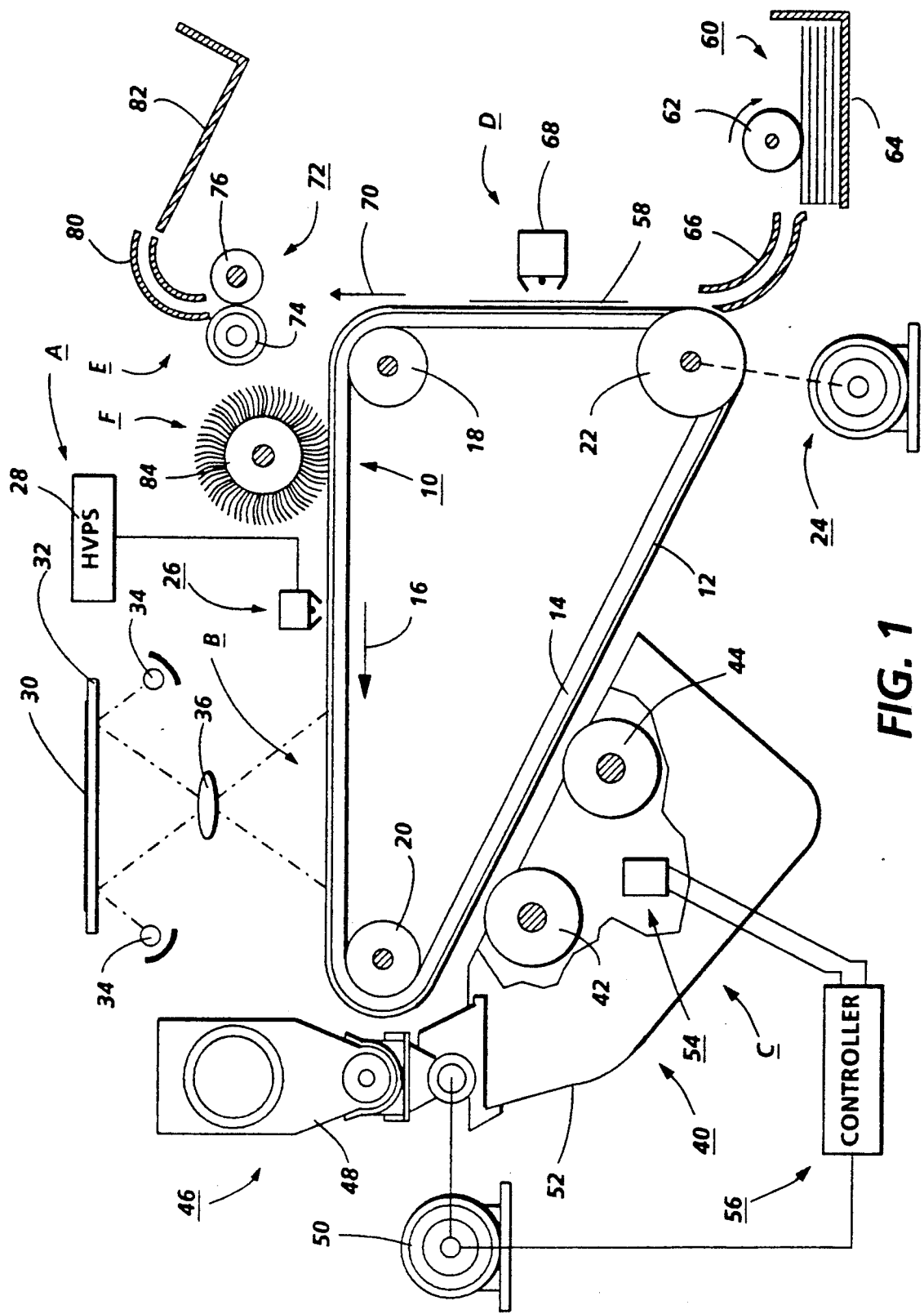
FIG. 1 is a schematic elevational view of an illustrative electrophotographic printing machine incorporating the apparatus of the present invention therein.

With reference to FIG. 1 there is shown an electrophotographic printing machine incorporating a belt 10 having a photoconductive surface 12 deposited on a conductive substrate 14. Belt 10 moves in the direction of arrow 16 to advance successive portions of photoconductive surface 12 sequentially through the various processing stations disposed along the path of movement thereof. Belt 10 is entrained about stripping roller 18, tension roller 20 and drive roller 22. Motor 24 rotates drive roller 22 to advance belt 10 in the direction of arrow 16. A pair of springs (not shown) resiliently urge tension roller 20 against belt 10, for maintaining it in tension.

Initially, a portion of belt 10 passes through charging station A at which a corona generating device 26, excited by a high voltage power supply (HVPS) 28, charges photoconductive surface 12 to a relatively high, substantially uniform potential. The charged portion of the photoconductive surface 12 is next advanced through exposure station B. At the exposure station B, an image of an original document 30 is supported upon a transparent platen 32 and is illuminated by lamps 34. Light rays reflected from the original document 30 are transmitted through lens 36 and focused onto the charged portion of the photoconductive surface 12 to selectively dissipate the charge thereon. This records an electrostatic latent image on the photoconductive surface corresponding to the informational areas contained within the original document.

After the electrostatic latent image has been recorded on the photoconductive surface 12, belt 10 advances the latent image to development station C. A magnetic brush development system 40 advances developer material into contact with the latent image. Preferably, magnetic brush development system 40 includes two magnetic brush development rollers 42 and 44. Each roller advances developer material into contact with the latent image. These developer rollers form a brush of carrier granules and toner particles extending outwardly therefrom. The latent image attracts toner particles from the carrier granules, forming a toner powder image on the latent image.

As successive latent images are developed, toner particles are depleted from the developer mixture. A toner particle dispenser 46 meters out toner particles from a container 48 in response to the energization of dispensing motor 50. The dispensed toner drops into developer housing 52 wherein it is mixed with the carrier granules. A sensor 54, which is the subject of this invention and shall be described in detail below, is positioned within the developer housing 52 adjacent to developer roller 42. The sensor 54 generates an electrical output signal indicative of toner concentration, which is transmitted to controller 56. Controller 56 generates an error signal which energizes dispensing motor 50 for dispensing toner particles. Thus, when the quantity of toner particles in the developer mixture is beneath a predetermined level a correction is made.

After the electrostatic latent image has been developed, belt 10 advances the toner powder image to transfer station D. A sheet of support material 58 is advanced to the transfer station D by sheet feeding apparatus 60. Preferably, the sheet feeding apparatus includes a feed roller 62 contacting the uppermost sheet of stack 64 and driving the sheet into guide 66. The support material exiting the guide contacts the surface of belt 10 in a timed sequence, so that the toner powder image is registered thereon. A corona generating device 68 sprays ions onto the back side of sheet 58 causing the toner powder image to be attracted from the photoconductive surface 12 to the sheet 58. After transfer, the sheet 58 continues to move with the belt 10 until it is stripped therefrom as the belt undergoes a sharp change in direction around stripping roller 18.

The sheet 58 is then advanced in the direction of arrow 70 to fusing station E including a fuser assembly 72 which permanently affixes the transferred powder image thereto. Preferably, fuser assembly 72 comprises a heated fuser roller 74 and back-up roller 76. The sheet 58 passes between rollers 74 and 76 with the toner powder image contacting fuser roller 74. In this manner, the toner powder image is permanently affixed to sheet 58. After fusing, the sheet is advanced through guide 80 to catch tray 82 for subsequent removal from the printing machine by the operator.

After the sheet of support material is separated from the belt 10, the residual toner particles adhering to the photoconductive surface 12 are removed therefrom at cleaning station F. Cleaning station F includes a rotatably mounted fibrous brush 84 in contact with the photoconductive surface. Subsequent to cleaning, a discharge lamp (not shown) floods the photoconductive surface with light to dissipate any residual electrostatic charge remaining thereon prior to the charging thereof for the next successive imaging cycle.

Figure 2:
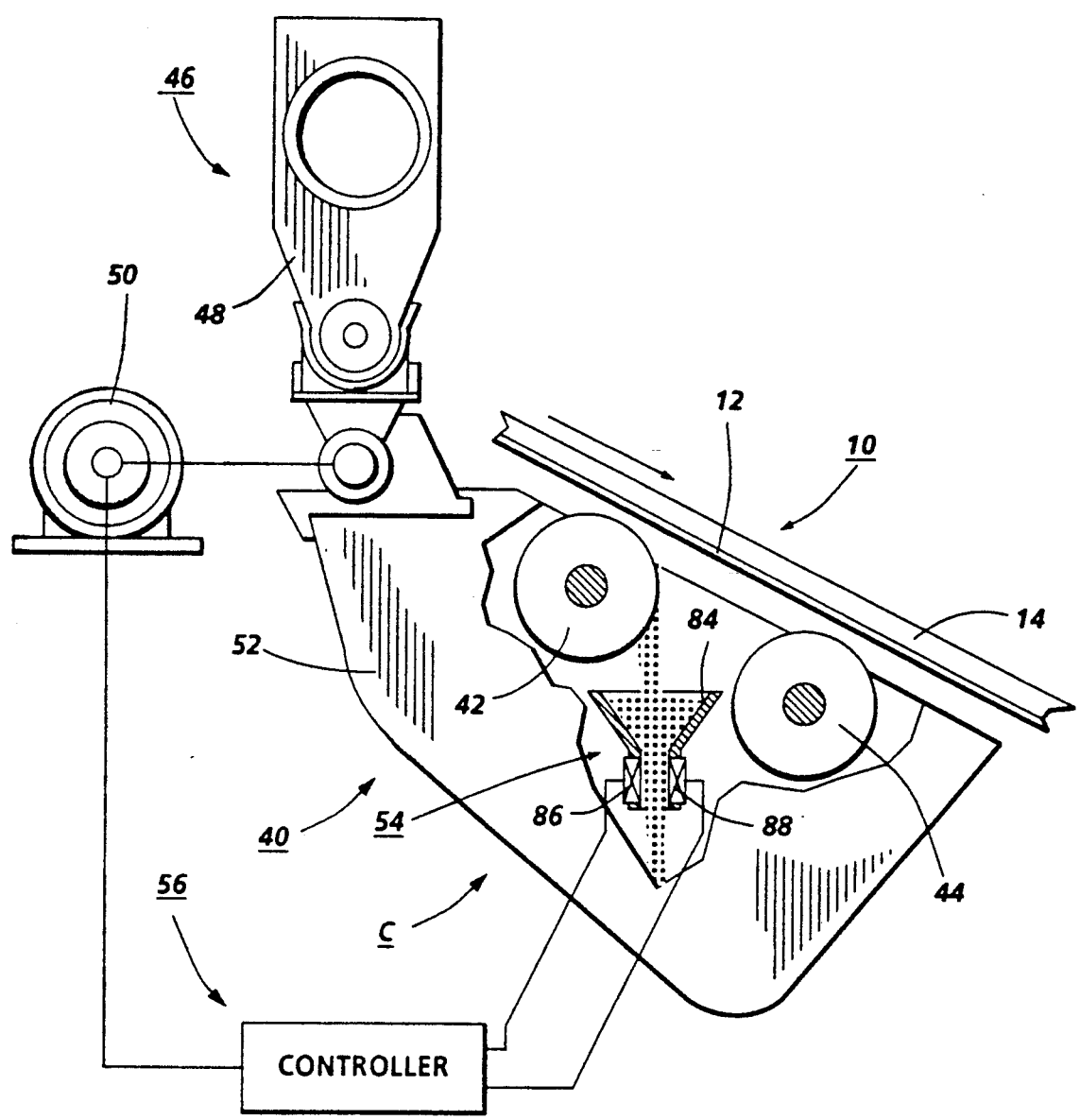
FIG. 2 is a schematic elevational view of a toner concentration sensor which could be used in the printing machine of FIG. 1.

It is believed that the foregoing description is sufficient to illustrate the general environment for a typical application of the present invention. In FIG. 2 the sensor 54 is is shown in greater detail. It comprises a chute 84 through which completely mixed two-component developer passes and is directed through the gap between the facing surfaces of a generating acoustic transducer 86 and a receiving acoustic transducer 88. A consistent flow rate through the gap should be maintained for accurate measurement. In an alternative configuration, a movable closure (not shown) at the dispensing end of the chute could be positioned to periodically provide a stationary sample of the developer mixture in the gap through which acoustic measurements could be taken.

The facing surfaces of the transducers 86 and 88 are separated by the gap distance (d). Preferably, the generating transducer is excited by a continuous sinusoidal wave at frequency (f). The distance (d) between the transducers and the acoustic frequency (f) should be chosen to allow a moderate attenuation of the acoustic wave that propagates through the air and toner filled carrier material. Some attenuation is desirable in order that multiply-reflected acoustic waves will have little influence on the received signal. For example, if the one-way attenuation of the acoustic wave across the gap distance (d) is 10 dB, the first multiply-reflected wave arriving at the receiving transducer 88 will be 20 dB below this, i.e., one tenth of the signal amplitude of the first received signal. Hence, the effect of reverberations within the sample will be small.

The acoustic wave phase velocity ($v_d$) through the developer is readily determined from the following equation by measuring the phase difference ($\Delta\Phi$) between the signal received by the receiving transducer and the excitation signal of the generating transducer.

$$\Delta\Phi = \frac{2\pi df}{v_d} \quad [\text{radians}] \qquad (4)$$

For small gaps (d), on the order of 1 to 4 mm, and an acoustic frequency (f), on the order of 100 kHz to 400 kHz, the received signal fortuitously will be phase shifted by a small number of cycles (on the order of about five or less). This allows an unambiguous determination of the phase difference ($\Delta\Phi$), notwithstanding the use of a continuous acoustic wave. Because the range of the expected value of the phase velocity ($v_d$) (i.e., between about 230 and 270 m/s), and precise knowledge of the quantities d and f are known, the total phase shift ($\Delta\Phi$) may be unambiguously determined from Equation 4 for total phase shifts of $2\pi n$, where n is on the order of 2 to 5.

It follows that the measurement of the "slow" wave phase velocity in a developer mixture may be a very sensitive tool for monitoring the toner concentration. Also, it is inherently noninvasive and very simple to perform, since the critical parameters of this measurement technique, such as acoustic frequency (f) and transducer spacing (d), are relatively easy to achieve with high accuracy. Measurement of the phase difference between the generating and receiving acoustic signals may be performed in any number of standard ways. Lock-in techniques would work very well, and could probably be implemented at reasonable cost for the frequency range anticipated. Alternatively, simple bandpass filtering of the received signal may be sufficient to allow simpler phase-detection techniques.

A brief description of one possible manifestation of the in situ concentration measurement technique is as follows. The developer system of interest has been previously measured for a number of toner concentration levels, in order to calibrate the system. The acoustic phase velocities, as a function of toner concentration (and frequency), may be stored in a look-up table. A continuous sinusoidal voltage $V_1$, of frequency (f) (on the order of 100 kHz to 400 kHz), is made to drive acoustic transducer 86. Receiving transducer 88 receives the acoustic wave that propagates through the developer in chute 84 and the voltage output $V_2$, of the receiving transducer, is detected. The distance (d) between the faces of the two transducers should be on the order of a few millimeters. The output voltage $V_2$ is fed into appropriate phase detection circuitry, using driving voltage $V_1$ as a reference signal. The phase of $V_2$, relative to $V_1$, ($\Delta\Phi$), is measured and will fall between $-\pi$ and $\pi$. If desired, the ratio of amplitudes $|V_1|/|V_2|$ may also be measured in order to yield information concerning the acoustic attenuation in the developer.

From Equation 4, a nominal value of the expected acoustic phase shift is determined for an expected nominal toner concentration, e.g. 6%. The "slow" wave phase velocity through the mixture is $v_d^{6\%}$, and the nominal phase shift $\Delta\Phi^{6\%} = 2\pi df/v_d^{6\%}$. The difference $\Delta\Phi - \Delta\Phi^{6\%}$ is taken and is normalized into the range of $-\pi$ to $\pi$ by substracting an integral number of $2\pi$s. If the normalized $\Delta\Phi$ is $>0$ it follows from Equation 4 that $V_d$ is smaller than the desired value $V_d^{6\%}$, and hence the toner concentration is too high. In this case no toner is added to the system, and perhaps some development without transfer to paper may be employed to reduce the concentration. Conversely, if the normalized $\Delta\Phi<0$, the controller will transmit a signal to motor 50 to add toner to the developer.

One should easily be able to measure the phase delay to within 0.01 radians. Thus, from Equation 4, assuming for example that d=2 mm, f=150 kHz, and the nominal acoustic wave velocity $v_d=250$ m/s, one could then measure a change in acoustic wave velocity of 0.33 m/s. For typical developer materials this would correspond to a change of about 0.05% in toner concentration.

Since environmental conditions such as temperature, atmospheric pressure, and humidity may effect the "slow" wave phase velocity $v_d$, as they effect the acoustic velocity in bulk air, it may be desirable, in some instances, to measure the "slow" wave phase velocity under a range of environmental conditions, creating a larger database of calibration values for the concentration measurement. Then, by measuring the appropriate parameter (e.g. relative humidity) simultaneously with the acoustic measurement, the toner concentration in the developer, for that particular set of environmental parameters may be inferred from a multi-parameter look-up table.

EXPERIMENTAL RESULTS

Figure 3:
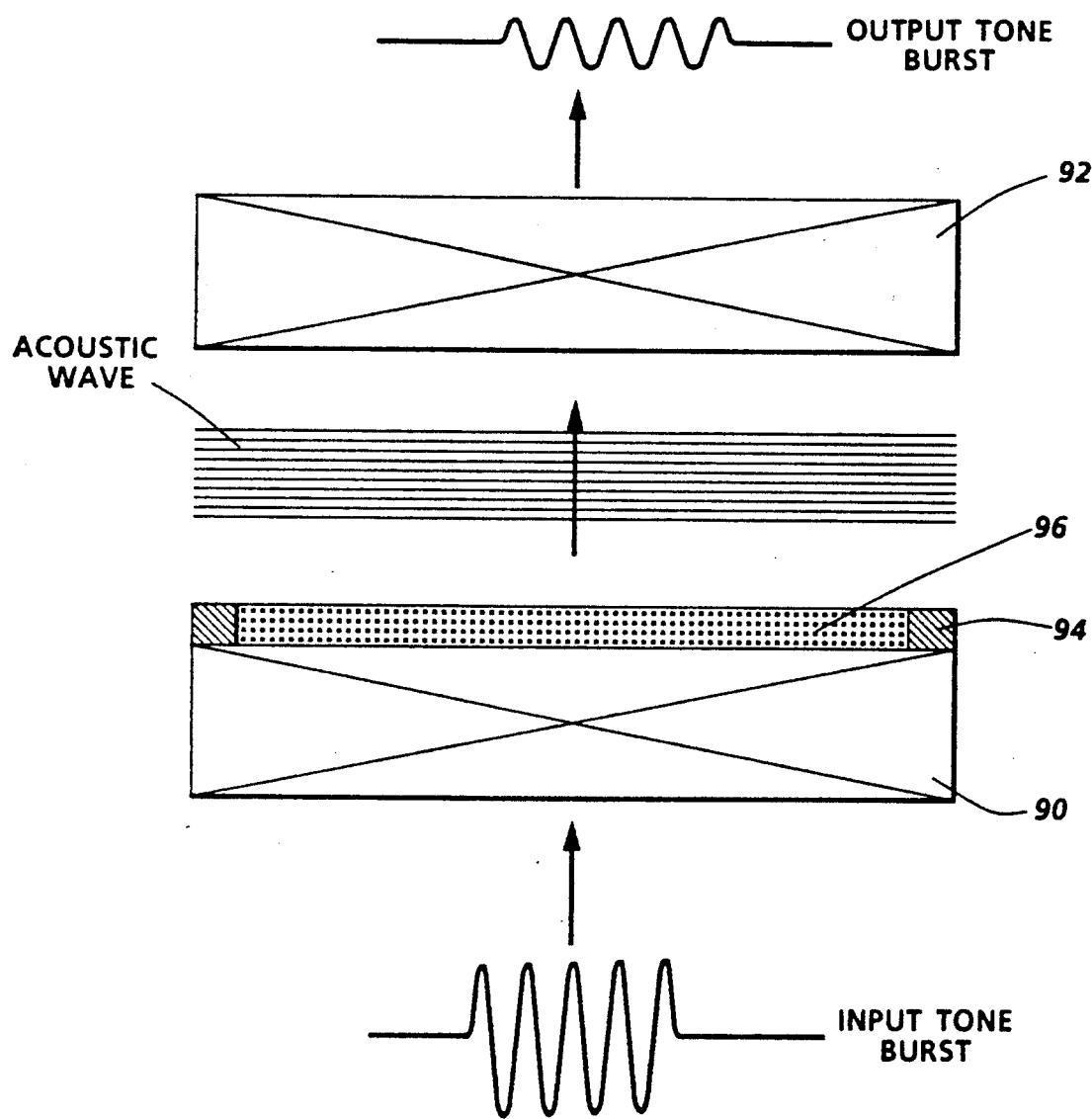
FIG. 3 is a schematic representation of an experimental test arrangement used to characterize the present invention.

Experimental results have validated this acoustic measurement technique for determining the toner concentration in a toner/carrier mixture. Mixtures of xerographic developer (using Xerox 1025 ® toner and carrier) of 0%, 2%, 4%, and 6% toner in carrier (percentage by mass) were fabricated. A test fixture was constructed as indicated in FIG. 3. It comprised two broadband Panametrics V301 acoustic transducers, a bottom generating transducer 90 and a top receiving transducer 92 placed opposite one another and spaced 13 mm apart. A 2 mm high metal ring 94 was attached to the bottom transducer 90, taking care not to cover the active portion of the transducer. A developer sample 96 could then be poured over the transducer, filling the volume within the ring and made level with the top thereof. Hence, a layer of developer, of known thickness (i.e. 2 mm), could be placed between the two transducers.

After a sample of known toner concentration was loaded in the ring 94, the generating transducer 90 was excited with a 40 µs tone burst signal, i.e., a gated sinusoidal signal, whose carrier frequency could be varied between 100 kHz and 400 kHz. These frequencies are well above the critical frequency ($f_c$) of about 13.5 kHz, typical for this developer mixture. The signals received at the receiving transducer were then measured.

Figure 4:
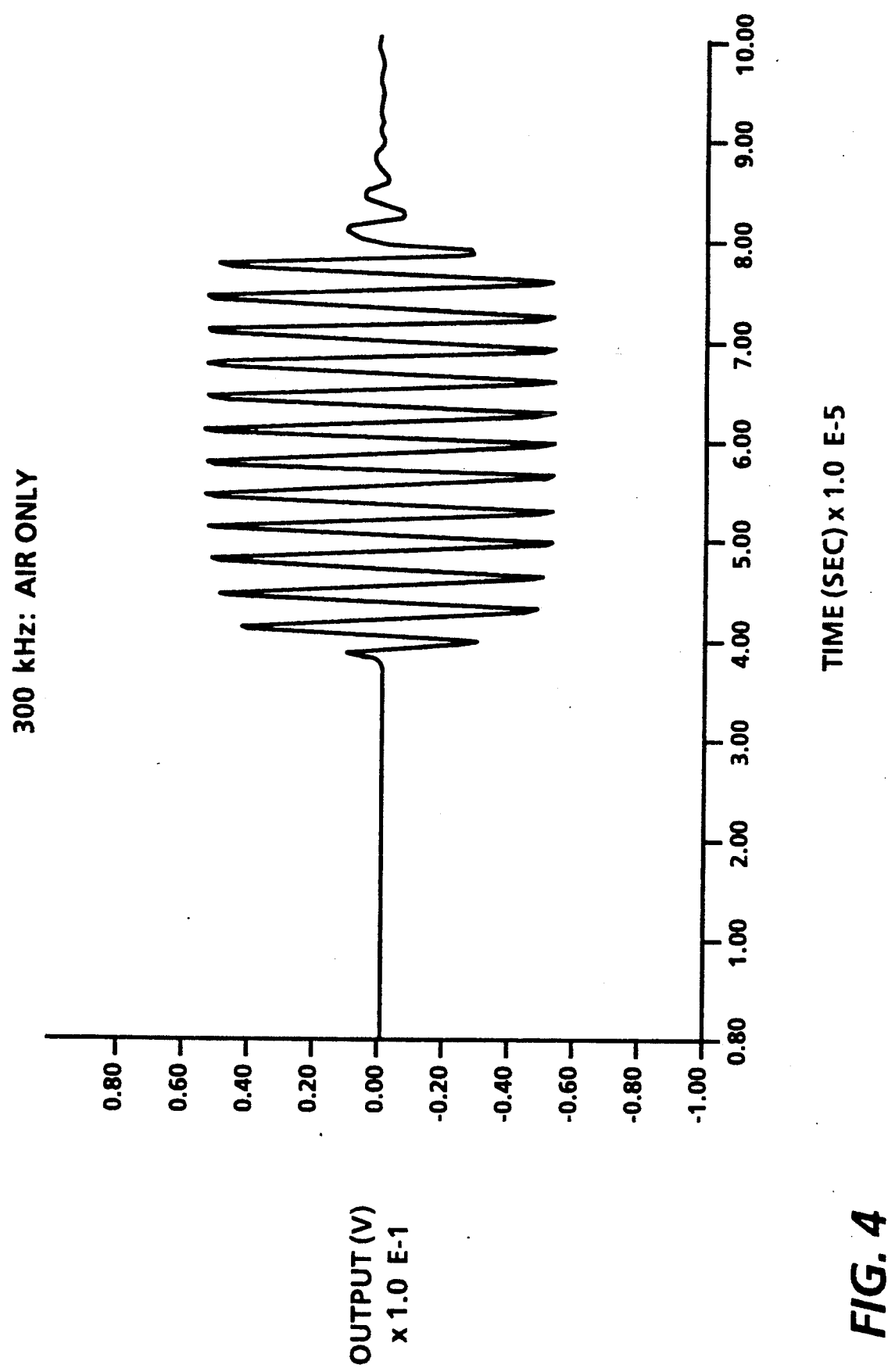
FIG. 4 is a plot of an acoustic tone burst signal, through air without an interposed toner sample, received in the test arrangement of FIG. 3.

To characterize the properties of an acoustic wave propagating through a known sample of developer, a measurement was first made with no developer material present, i.e., only air filled the region between the transducers 90 and 92. In FIG. 4 there is shown the plot of a typical acoustic waveform received at the receiving transducer, with only air present between the bottom and top transducers, at an acoustic frequency (f) of 300 kHz. Excitation of the generating transducer 90 originates at t=0, so that the approximately 40 µs delay in the signal reaching the receiving transducer 92 is due to the propagation time of the acoustic wave between the transducers. This propagation time (T), between transducers spaced apart by a distance (d), is directly related to the acoustic phase velocity in air ($v_{air}$), where $T = d/v_{air}$.

Figure 5:
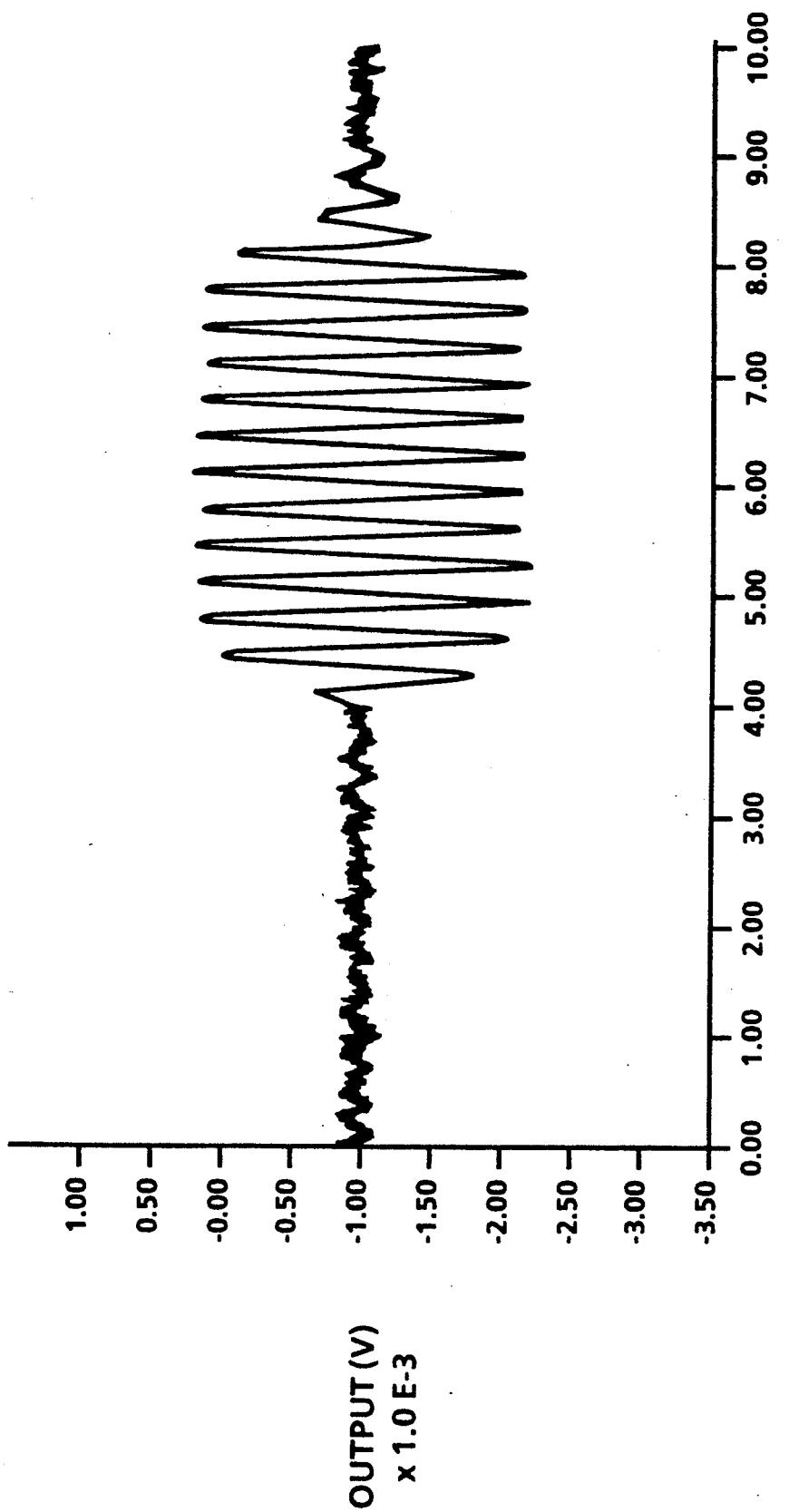
FIG. 5 is a plot of an acoustic tone burst signal, through air with an interposed toner sample, received in the test arrangement of FIG. 3.

Next, a developer sample 96 of known toner concentration was loaded into the ring 94 and the transducer was again excited with a 40 μs tone burst signal. The received signal is represented in the plot of FIG. 5 for a 6% toner concentration sample. It should be noted that the plots of FIGS. 4 and 5 represent the averaging of several hundred waveforms, to improve the signal-to-noise ratio.

Two important features were observed from a comparison of the results of FIGS. 4 and 5. First, the received acoustic signal, as represented in FIG. 5, is delayed by approximately 3.7 μs with respect to that of FIG. 4. This confirms that it takes longer for the acoustic wave to propagate through the 2 mm of the developer mixture than it takes to propagate through 2 mm of air. Second, the large attenuation of the acoustic wave through the developer mixture is indicated by the difference in the scales of the voltage signals between the two plots ($10^{-1}$ vs. $10^{-3}$). The maximum average amplitude of the signal of FIG. 4 is about 0.05 volts as compared to the maximum average amplitude of the signal of FIG. 5 of about 0.0002 volts. Thus, the received acoustic signal, through the 6% toner concentration developer mixture, is about 250 times smaller than through air. Both the shift in acoustic phase velocity and the large attenuation are parameters which are useful in discerning the toner concentration.

Figure 6:
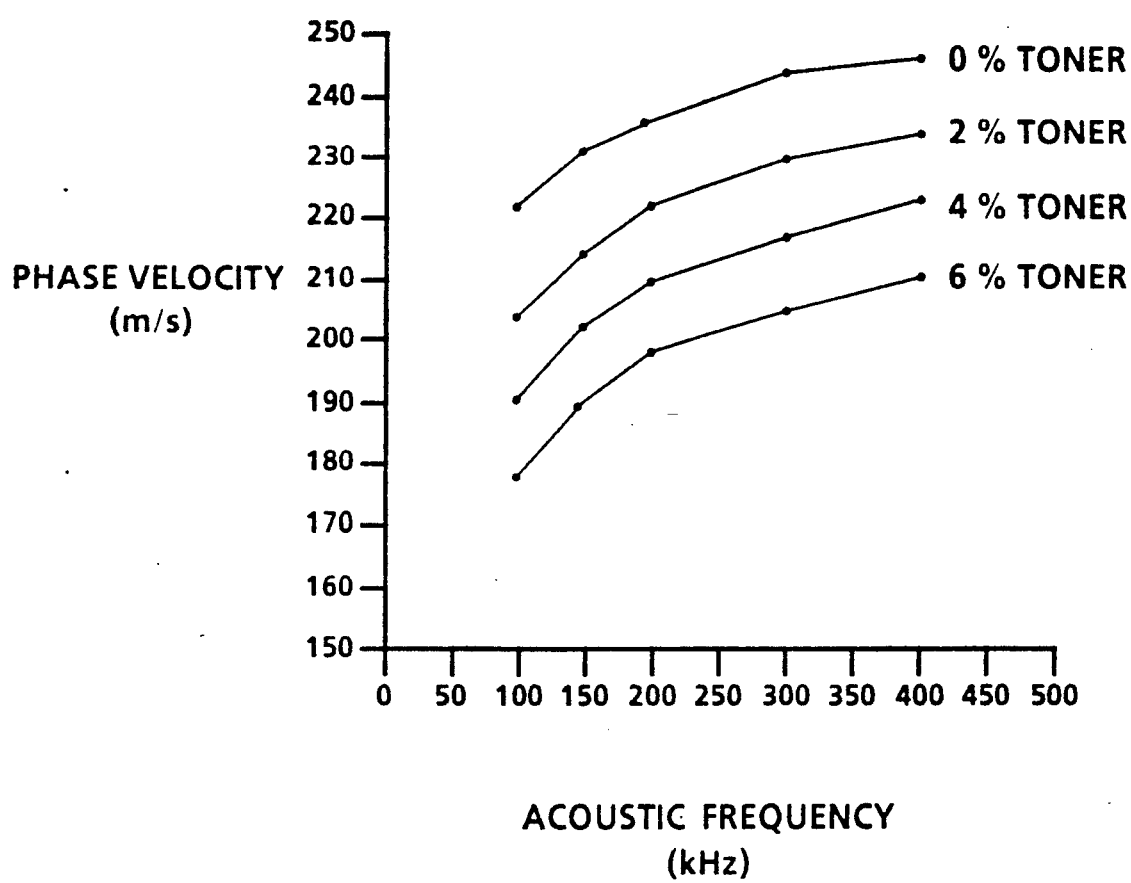
FIG. 6 is a family of curves showing the relationship of acoustic phase velocity, acoustic frequency and toner concentration.
Figure 7:
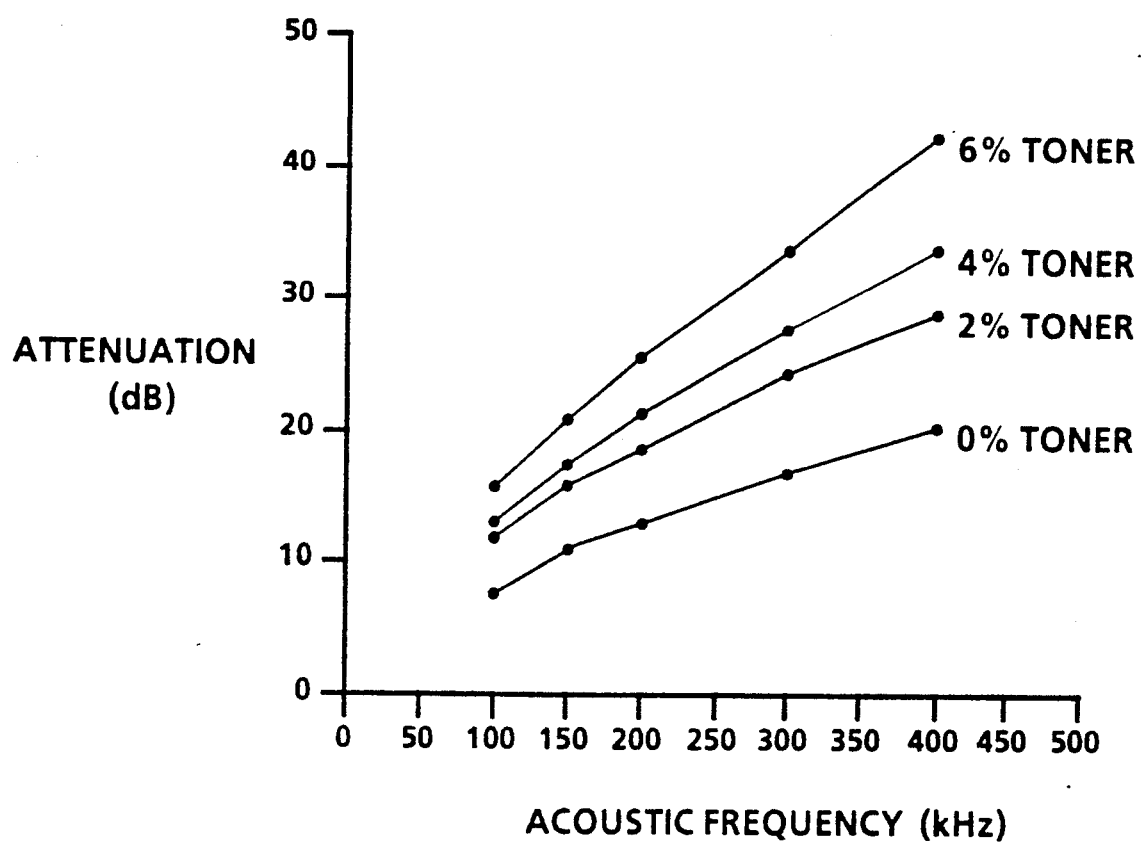
FIG. 7 is a family of curves showing the relationship of acoustic attenuation, acoustic frequency and toner concentration.

Measurements, as described above, were performed for each of the four toner concentrations, over a range of acoustic frequencies. The results are shown in FIGS. 6 and 7. In FIG. 6 acoustic wave phase velocity is plotted as a function of acoustic frequency through developer mixtures of different toner concentrations. It can be observed that the phase velocity decreases monotonically, and appears to decrease approximately linearly, with increasing toner concentration at all frequencies used in the experiment. The effect is on the order of about −6 m/s per percent toner concentration. In FIG. 7 attenuation of the acoustic wave amplitude (in dB) is plotted as a function of acoustic frequency through developer mixtures of different toner concentrations. Attenuation is seen to increase with acoustic frequency and with toner concentration, increasing more rapidly with frequency, as the toner concentration increases. The physical reason for this attenuation is not at present clear, as it is not predicted in the standard theories. As mentioned above, the attenuation may be expected to limit the upper frequency at which a practical measurement may be made.

From FIGS. 6 and 7, it is evident that the acoustic wave displays good sensitivity to the concentration of toner in a two-component developer mixture and that toner concentration could be measured either by changes in the received signal acoustic phase velocity or by changes in the received signal attenuation. This sensitivity clearly originates in the changes in the mechanical properties of the developer, in particular the tortuosity, which may be related to the porosity of the mixture.

ALTERNATIVE EMBODIMENT

Figure 8:
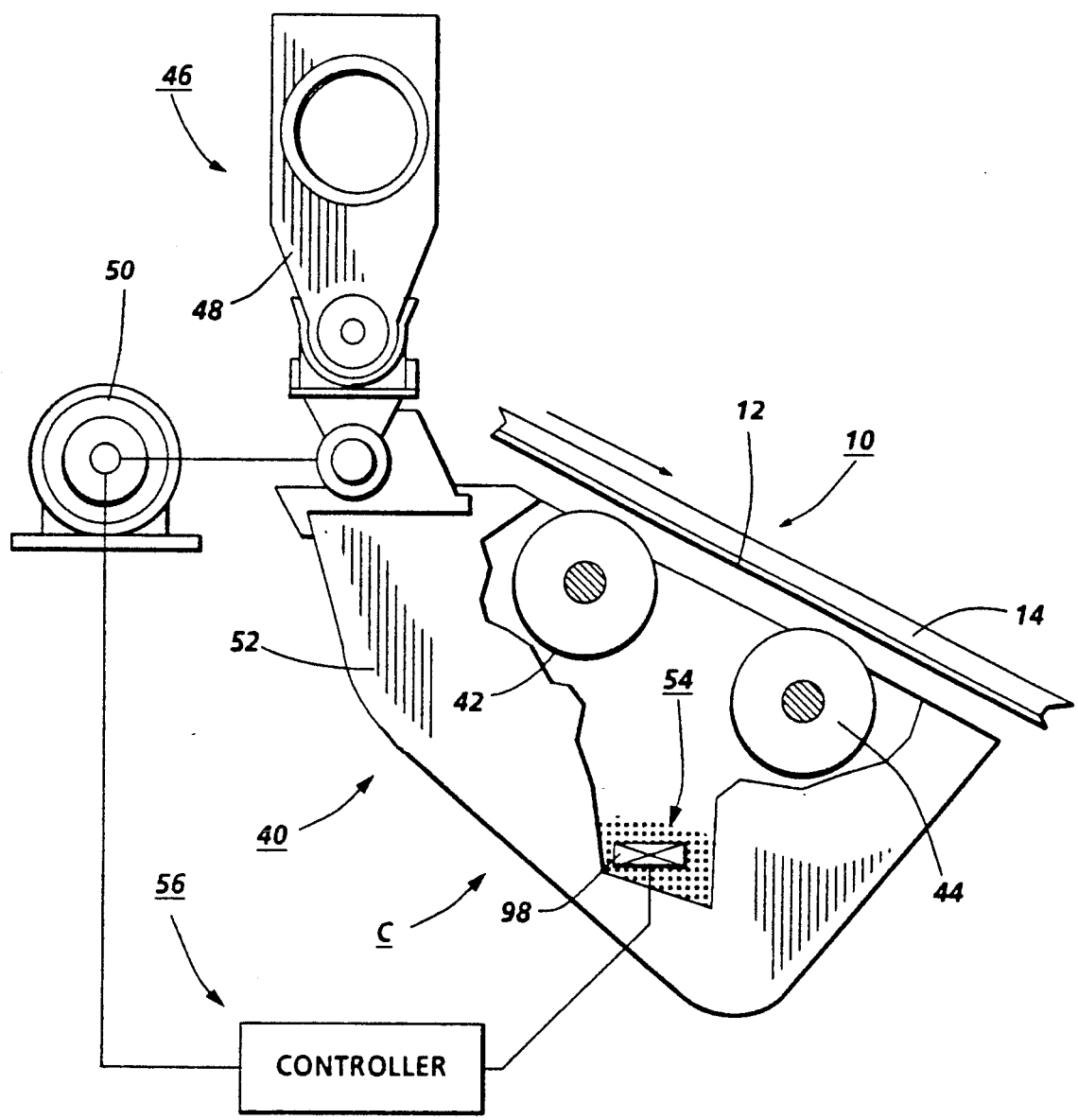
FIG. 8 is a schematic elevational view of an alternative configuration of a toner concentration sensor which could be used in the printing machine of FIG. 1.

In an alternative embodiment of this invention, illustrated in FIG. 8, a single acoustic transducer 98 may be used. It is configured as a resonating element by introducing positive electrical feedback thereto. The resonance frequency is determined by the reactance and resistance of the electrical circuit that drives the transducer as well as the electrical input impedance of the transducer itself. It is well known that the electrical input impedance of an acoustic transducer is a function of the acoustic impedance of the material that loads the transducer. Hence, the material that mechanically loads a transducer will effect the resonant frequency thereof. In the present instance, the single acoustic transducer 98 would be configured as a resonator so that its resonant frequency might be on the order of 100 kHz. The transducer, or at least its resonating surface, would be immersed in a well mixed sample of the multi-component developer mixture within the developer housing 52. As the acoustic impedance (directly related to the acoustic velocity and attenuation coefficient) of the developer mixture is altered by changes in the toner concentration, the resonant frequency of the transducer will be shifted. As the controller 56 monitors the resonant frequency, error signals would be generated in response to deviations from the desired toner concentration, so as to increase the amount of toner dispensed into the developer mixture.

It may be useful to use two resonators in this configuration in order to cancel out effects of temperature, atmospheric pressure, or humidity drift on the measurement. The second resonator would not be in contact with the developer mixture, but would remain entirely air-backed so that the resonant frequency of the transducer in contact with the developer mixture would be compared with this second air-backed transducer.

It should be understood that numerous changes in the process steps, the details of construction, and the combination and arrangement of elements and materials may be resorted to without departing from the true spirit and scope of the invention as hereinafter claimed.

What is claimed:

1. A method for measuring a sample of a porous material having a gaseous fluid and fine granular material located within its pores, and for determining the concentration of the fine granular material within the sample, comprising the steps of
   generating a first acoustic wave signal of known amplitude and phase velocity,
   directing said first acoustic wave signal through said sample,
   receiving a second acoustic wave signal representing said first acoustic wave signal having passed through said sample, and
   determining the concentration of said fine granular material in said sample from the changes between said first acoustic wave signal and said second acoustic wave signal.

2. The method of claim 1 wherein said step of determining the concentration is achieved by ascertaining the attenuation of said second acoustic wave signal by the difference in amplitude of said signals.

3. The method of claim 1 wherein said step of determining the concentration is achieved by ascertaining the difference in the phase velocities of said signals.

4. The method of claim 1 wherein said porous material is a larger diameter granular material.

5. The method of claim 4 wherein said sample is a xerographic developer mixture, said larger diameter granular material is carrier, said fine granular material is toner, and said gaseous fluid is air.

6. A method for measuring a sample of porous material having a gaseous fluid and fine granular material located within its pores, and for determining the concentration of the fine granular material, comprising the steps of
- providing an acoustic transducer having a known resonant frequency,
- immersing said acoustic transducer within said sample, whose acoustic impedance is altered by changes in the concentration of said fine granular material therein,
- exciting said acoustic transducer to resonate,
- monitoring the resonant frequency of said immersed acoustic transducer, and
- determining the concentration of the fine granular material in said sample from changes in the resonant frequency.

7. A method for measuring a porous material having a gaseous fluid and fine granular material located within its pores, and for determining the concentration of the granular material, comprising the steps of
- providing an acoustic transducer,
- exciting said acoustic transducer to generate acoustic wave signals,
- directing said acoustic waves into said porous material having a gaseous fluid and fine granular material located within its pores, and
- determining the concentration of the fine granular material in response to alterations in said acoustic wave signals indicative of changes in acoustic wave phase velocity and attenuation of the acoustic wave signals.

8. Apparatus for measuring a sample of a porous material having a gaseous fluid and fine granular material located within its pores, and for determining the concentration of the fine granular material within the sample, comprising
- means for generating a first acoustic wave signal of known amplitude and phase velocity,
- means for directing said first acoustic wave signal through said sample,
- means for receiving a second acoustic wave signal representing said first acoustic wave signal having passed through said sample, and
- means for determining the concentration of said fine granular material in said sample from the changes between said first acoustic wave signal and said second acoustic wave signal.

9. Apparatus for measuring a sample of porous material having a gaseous fluid and fine granular material located within its pores, and for determining the concentration of the granular material, comprising
- an acoustic transducer having a known resonant frequency immersed within said sample, the acoustic impedance of said acoustic transducer being altered by changes in the concentration of said fine granular material within said sample,
- means for exciting said acoustic transducer to resonate,
- means for monitoring the resonant frequency of said immersed acoustic transducer, and
- means for determining the concentration of the fine granular material in said sample from changes in the resonant frequency.

* * * * *